United States Patent [19]

McDowell

[11] Patent Number: 4,620,930

[45] Date of Patent: Nov. 4, 1986

[54] PROCESS FOR RAPIDLY DETERMINING BIOLOGICAL TOXICITY OF WASTEWATER

[75] Inventor: Curtis S. McDowell, Allentown, Pa.

[73] Assignee: Polybac Corporation, Allentown, Pa.

[21] Appl. No.: 794,521

[22] Filed: Dec. 16, 1985

[51] Int. Cl.$^4$ .................... C02F 3/12; C12M 1/36; G01N 33/18; C12Q 1/18

[52] U.S. Cl. .................... 210/614; 210/611; 436/62; 436/138; 435/32

[58] Field of Search .................... 435/32, 33; 436/62, 436/127, 131, 130, 138; 210/614, 96.1, 620, 611

[56] References Cited

U.S. PATENT DOCUMENTS

| | | | |
|---|---|---|---|
| 3,510,407 | 5/1970 | Stack, Jr. | 436/62 |
| 3,981,777 | 9/1976 | Alsop | 435/32 |
| 4,162,195 | 7/1979 | Solyom et al. | 435/32 |
| 4,329,232 | 5/1982 | McKenna | 436/62 |
| 4,564,444 | 1/1986 | Hiraoka et al. | 210/96.1 |
| 4,564,453 | 1/1986 | Coplot et al. | 436/62 |

FOREIGN PATENT DOCUMENTS

| | | | |
|---|---|---|---|
| 0006376 | 1/1980 | European Pat. Off. | 435/32 |
| 54-44595 | 4/1979 | Japan | 210/614 |
| 1017687 | 5/1983 | U.S.S.R. | 435/32 |

Primary Examiner—Benoit Castel

[57] ABSTRACT

This invention pertains to a method for analyzing the biochemical decomposibility of aqueous substrates by microorganisms and particularly to a method for analyzing the quality or biological toxicity of incoming sewage to a sewage disposal plant. The process comprises: placing a preselected amount of bacterial culture, in the form of a dried powder, in contact with a preselected amount of aqueous waste containing greater than 5 mg/l dissolved oxygen, the bacterial culture being capable of effecting aerobic biodegradation of organic waste; measuring the dissolved oxygen content of the aqueous waste during rehydration and respiration development of the microorganisms as a function of time; determining the rate of dissolved oxygen decline at a preselected time; and then comparing the rate of dissolved oxygen decline to the rate of dissolved oxygen for a preselected baseline standard substrate. By comparing the ratio of dissolved oxygen decline at a preselected time with respect to a test sample and a standard substrate one can calculate the relative toxicity or inhibition of the incoming sewage to aerobic respiration and growth.

6 Claims, 3 Drawing Figures

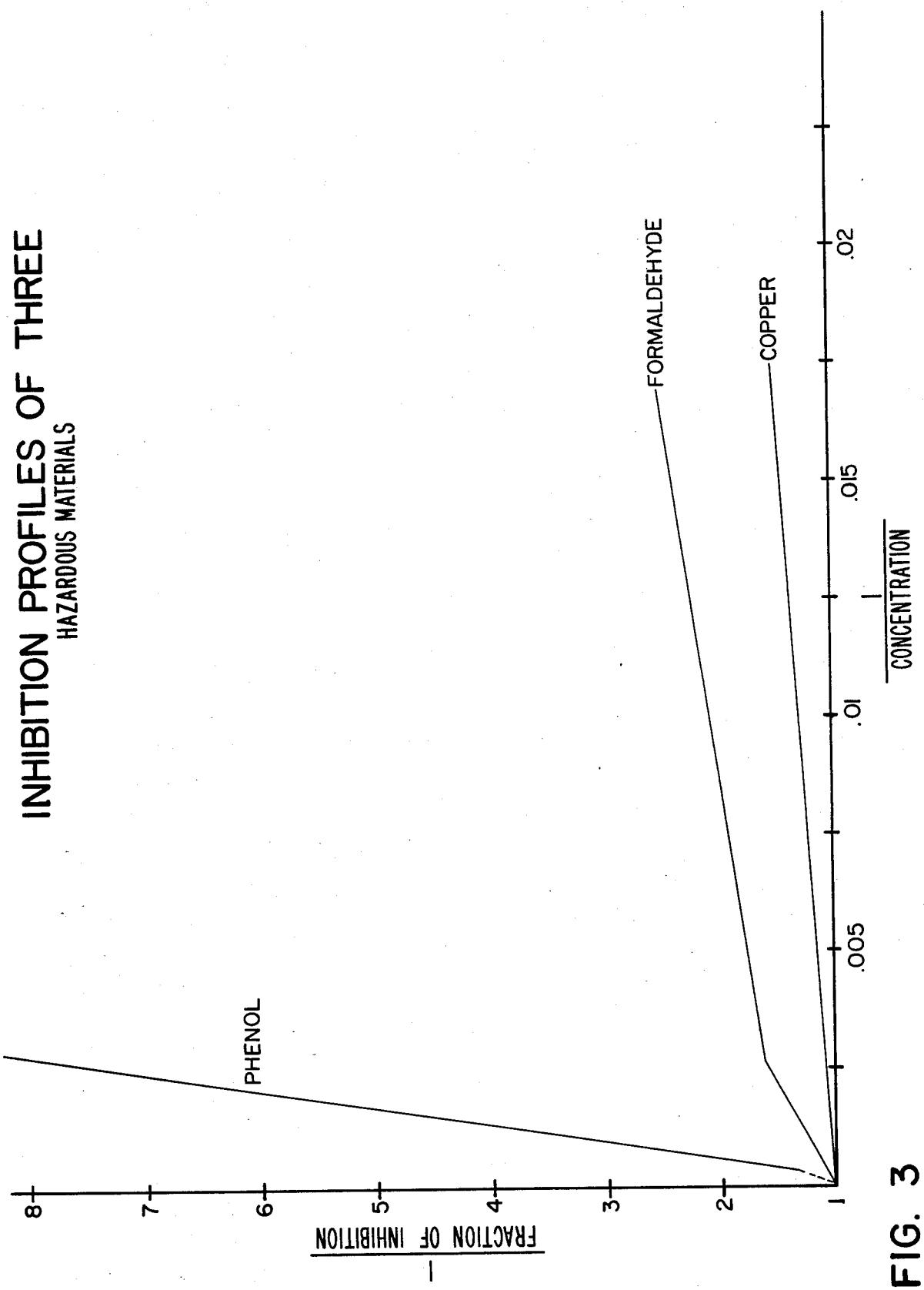

PROCESS FOR RAPIDLY DETERMINING BIOLOGICAL TOXICITY OF WASTEWATER

TECHNICAL FIELD

This invention relates to a process for determining the biological decomposibility or toxicity of wastewater to a sewage treatment facility and to a process for determining the organic content of the aqueous system.

BACKGROUND OF THE INVENTION

The biological processing of organic waste in industrial and municipal wastewater streams has long been known. Although these biological systems typically utilize microorganisms to effect biochemical decomposition of the organic waste, the processing plants may differ in the method in which the microorganisms are cultivated. In one type of system, such as an activated sludge process, the microorganisms are dispersed in an aqueous medium and decomposition effected with the microorganisms in the dispersed state while in another type, commonly referred to as a fixed film process, the microorganisms are confined and the contaminated wastewater allowed to pass in contact with the fixed film containing microorganisms.

Microorganisms, whether dispersed or carried on fixed films in sewage treatment plants, are quite vulnerable to a variety of chemicals and vulnerable to the quality of incoming sewage, in terms of chemical content. Such chemicals and sewage may drastically alter the performance characteristics of the microorganisms. In some instances where there are industrial spills, etc., the spill itself may raise the concentration of various chemical components in the sewage to a sufficient level to kill the microorganisms in the biological treatment plant, and in effect, render the plant inactive. In view of the somewhat delicate nature of microorganisms it is highly desirable to monitor the quality of incoming sewage to a plant so that appropriate action can be taken prior to introduction of the sewage to the plant. In addition, it is desirable to detect toxic substances so that appropriate action can be taken upstream of the biological treatment process to prevent the plant from shutting down. In that way one can maintain biological activity at a desired level.

A variety of test procedures have been developed for analyzing the quality of sewage for the purpose of determining the toxicity of the sewage, for determining the total chemical content in the sewage, and to determine the oxygen consumption rate of the microorganisms in that sewage. By and large many of the analytical processes have involved the utilization of complicated equipment or have taken a substantial amount of time in order to complete the test and obtain meaningful results. In many cases, because of the time required to obtain the results, sufficient time has not been provided to take appropriate action with respect to the handling of the incoming sewage. As a result, the plants in many cases were rendered inactive. Numerous patents have been issued which disclose various analytical processes for monitoring the quality of sewage. Some of these patents include:

U.S. Pat. No. 3,684,702 discloses a test procedure for determining the biochemical decomposibility of incoming sewage so as to effectively control the decomposition of the sewage under optimum conditions. The analytical technique comprises first isolating predetermined quantities of sewage, activated sludge, etc., then mixing the various quantities of sewage water containing activated sludge in an analysis fermentor and measuring the biological oxygen of the fermentors. This demand is then recorded and the measurements converted to control signals to control the recycling of activated sludge of the plant.

U.S. Pat. No. 4,329,232 discloses a process for rapidly determining the viable organism content in a wastewater treatment system. The test procedure involves aerating a suspension of biomass to be tested until the dissolved oxygen content reaches about 6 mg oxygen/liter and then determining an Oxygen Uptake Rate (OUR) as a function of time. This Oxygen Uptake Rate is then compared to another Oxygen Uptake Rate for a biomass sample which has been aerated and suspended in a standard substrate as above.

U.S. Pat. No. 3,635,564 discloses a quantitative measurement for determining the organic material contained in an aqueous solution and primarily for determining the effectiveness of a wastewater treatment process. The analysis technique described required the measurement of the refractive index and electrical conductivity of the water test sample in relation to the refractive index and electrical conductivity of a known solution. The difference between the refractive index and electrical conductivity of the unknown sample is correlated with respect to known systems containing various organic content. Earlier processes used COD and BOD analysis which requires a substantial amount of time.

U.S. Pat. No. 3,567,391 discloses a method for analyzing the biological oxygen demand in wastewater, and the process involved the use of a pyrolsis chamber functionally connected to a hydrogen flame ionization dectector. Like U.S. Pat. No. 3,635,564 and many prior art processes, this process involved the direct measure of respiratory oxygen requirement of bacteria in the sample.

U.S. Pat. No. 3,510,407 discloses a method for determining the amount of oxygen that will be consumed in the stabilization of organic material in a biological treatment system. The process involves measuring the rate of oxygen consumption at successive times until the rate of oxygen consumption assumes a substantially steady state, that state which is representative of auto-oxidation. The Oxygen Uptake Rate is then integrated as a function of time.

U.S. Pat. No. 3,224,837 discloses various prior art techniques for the determination of organic substances in water utilizing the measure of biological oxygen demand by a bacterial culture and acknowledged these methods were troublesome and time consuming. An electrolytic process is shown wherein organic impurities in the aqueous medium are oxidized to carbon dioxide and the carbon dioxide content measured. The carbon dioxide content is then correlated to organic content.

U.S. Pat. No. 3,731,522 discloses that it was common practice to measure oxygen consumption rate in sewage by activated sludge in order to determine the rate of bacterial growth. The patentees noted the five-day biological demand test as one of the most common and acknowledged that this analytic technique was unduly time consuming and did not provide sufficiently rapid results to enable alteration of processing of the sewage. To summarize, the prior art has utilized a variety of processes to determine the quality of sewage and its effect on a biological treatment system. Processes which have relied on the use of biological testing of the sewage typically have been inaccurate, not reproducible, and time consuming. Other tests which may have been quicker to run and more reliable in determining quantitative organic content, etc., often do not reflect the impact the particular organic will have on the microorganisms.

SUMMARY OF THE INVENTION

This invention pertains to a process for analyzing the quality of wastewater. The process is capable of providing analytical information with respect to the toxicity of incoming sewage to a waste disposal plant, to the quantity of organic component in the sewage, and to the type of toxic material in a particular system in an efficient and quick manner. In this process, a preselected amount of a special bacterial culture capable of aerobic biodegradation of organic waste is placed in a first test vessel containing a preselected amount of test wastewater containing at least 5 mg/l of dissolved oxygen. This bacterial culture is in the form of a dried powder and is added in a preselected amount. Once the bacterial culture is added and dispersed in the first test vessel, the dissolved oxygen content of the sample is measured as a function of time. A rate of dissolved oxygen decline is then determined at a preselected time. This rate of dissolved oxygen decline for the test wastewater is then compared against the rate of dissolved oxygen decline for a standard aqueous substrate. The ratio between the rate of decline of the test wastewater sample and standard aqueous substrate is proportional to the degree of inhibition of bacterial respiration or growth.

By the utilization of a specially prepared bacterial culture in the form of a dried powder and through the measurement of dissolved oxygen content, one can achieve several advantages which have not been available with prior processes. Some of these advantages include:

a rapid biological test for determining the toxicity of a wastewater sample;

a rapid, reproducible biological test for determining the toxicity of a specific chemical as a function of its concentration in water;

a rapid method of assessing the toxicity of acidic or basic solutions of various specific chemicals, organic and inorganic compounds to bacteria, and a rapid method of determining the effects of pH, temperature and/or dissolved gas such as $H_2S$, $NH_3$ and $CO_2$ on bacteria.

THE DRAWINGS

FIG. 3 is a plot of data showing toxic or inhibitory effects on biological systems of several chemicals as a function of the concentration of each chemical.

DETAILED DESCRIPTION OF THE INVENTION

Figure 1:
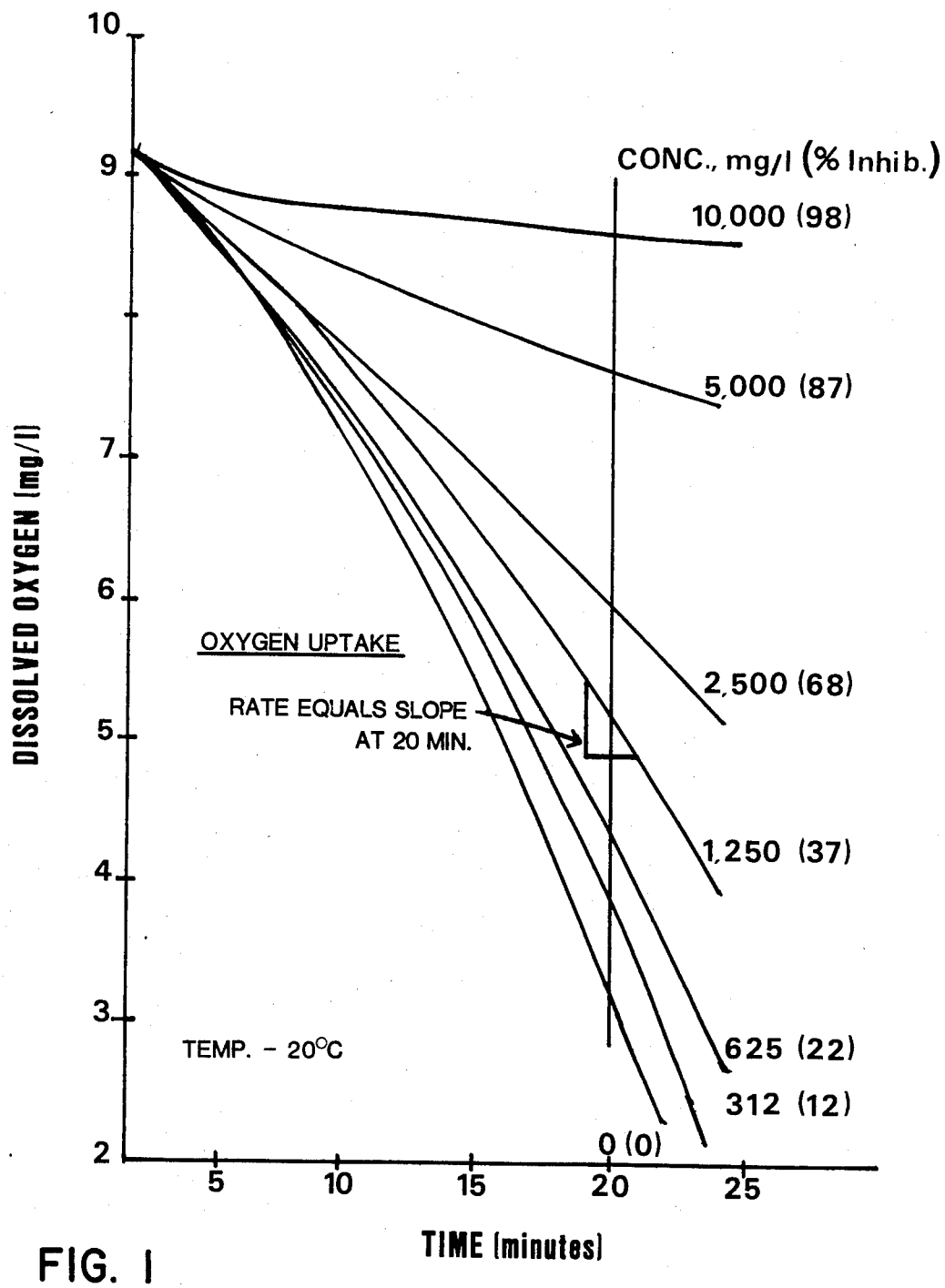
FIG. 1 is a plot of dissolved oxygen content as a function of time for aqueous systems containing various quantities of phenol.

The test procedure for determining the quality of an aqueous system containing waste organic material, particularly the quality of incoming sewage to a sewage plant, relies on the use of a dried, select adapted bacterial culture. Such cultures are specially geared to the biodegradation (i.e., chemical to protein conversion) of organic chemicals in both industrial and domestic wastewater. The dried cultures should be suited for the decomposition of organic wastes such as those wastes containing benzene, nitrotoluene, chlorinated benzenes, glycerine, aldehydes, cresols, petroleum products such as, kerosene, and phenols. In the decomposition of organics these select aerobic or facultatively anaerobic microorganisms utilize oxygen to generate energy to sustain the life function of the bacteria. The dried bacterial culture systems include bacteria species such as: pseudomonads SP, aerobacter SP, arthrobacter SP, bacillus SP, micrococcus SP, azotobacter SP, nocardia SP, and mixtures or blends. Commercially available dried cultures of the type suitable for the purpose of this rapid toxicity test include PHENOBAC®, FILABAC®, sold by Polybac Corporation, and other commercially available dry bacteria cultures.

In the rapid toxicity test described herein the dried culture first undergoes rehydration and then respiration development when contacted with aqueous system containing organic material. It is believed the methodology which involves exposure of the bacterial culture to specific organic components in sewage during both the rehydration and respiration development provides a particularly sensitive test for determining the toxicity or inhibitory characteristics of the wastewater. This exposure of the microorganisms or bacterial culture to the organic components during the rehydration process, as opposed to exposure after rehydration, not only enhances sensitivity, but allows the analysis of the wastewater to be completed in a much shorter length of time.

In carrying out the test process, a preselected amount of the dried bacterial culture is first charged to a preselected amount of a standardized substrate for the purpose of determining a standard of respiration or activity of the culture. The preselected quantity of bacteria used in carrying out the test will influence the rate of oxygen decline in the test sample. A sample containing a large quantity of bacterial culture will have a greater rate of oxygen decline than will the same sample having a lesser quantity. Typically, the quantity of bacterial culture is selected to give a good rate of oxygen decline, e.g., a decline of 2-5 mg/liter oxygen over a twenty minute interval. For reference purposes from 5 to 15 grams of culture/500 ml. of sample solution will be sufficient. The standardized substrate used in the test procedure is distilled waste or another standardized medium of known composition. On addition of the standardized substrate, the bacterial culture will rehydrate rapidly as a function of time. During this period, this oxygen respiration activity is measured by measuring the dissolved oxygen content in the substrate. The dissolved oxygen content then is plotted as a function of time. The rate of decline of dissolved oxygen content in the substrate is ascertained at some preselected time where the rate of dissolved oxygen decline is substantial and where the residual oxygen in the sample of greater than 0.5 mg/l oxygen. With bacterial cultures of the type described, this preselected time can be within the range of 10 to 30 minutes. In addition, the rate of decline is relatively constant over this period, thus giving an accurate reading. Although numerous methods can be used to ascertain the rate of decline of oxygen, the simplest is to determine that rate from a graph by taking the slope (y/x) of the curve at the preselected time.

The organic quality of sewage, in terms of organic content or toxic substance, is measured by repeating the exact same process, using the test sample in place of the standardized sample. In many instances, particularly where the test sample contains a substantial amount of toxic material or organic matter, the test sample may be diluted with distilled water to provide a more accurate measurement. This is done in those cases where the slope of the curve is small. In any event, the test substrate or wastewater to be tested is added to the test vessel containing the bacterial culture and the dissolved oxygen content measured as a function of time. The rate of decline in dissolved oxygen content for the test substrate or wastewater is then determined at the same preselected time utilized for the standard. This rate of decline is then compared to the rate of decline for the standardized substrate. The relative toxicity or inhibition of the test water versus the standardized substrate, can then be calculated by the equation:

$$\% \text{ Inhibition} = \left[1 - \left(\frac{\text{oxygen rate decline test sample}}{\text{oxygen rate decline standard}}\right)\right] \times 100$$

One of the advantages achieved through the determination of percent inhibition is an ability to determine the quantity of toxic material in the wastewater. This can be accurately determined by generating a set of inhibition curves for a specific toxic material. The inhibition curves are developed through a process which involves calculating the percent inhibition exhibited by a series of solutions of the selected test material of increasing concentrations. Percent inhibition is then plotted against concentration of the particular component. When a subsequent test sample is analyzed, and a percent inhibition value obtained for a sample containing an unknown quantity of the specific organic material, the concentration of that component can be obtained from the graph.

The following examples are provided to illustrate various emodiments of the invention.

EXAMPLE 1

Baseline Run

A baseline standard was generated for a bacterial formulation sold under the trademark PHENOBAC by Polybac Corporation by first charging 350 ml of distilled water to a first vessel. The water was then saturated with oxygen by sealing the vessel which was half full of air and shaking it rapidly. The dissolved oxygen content of the sample was then measured to determine if the oxygen level exceeded 5.0 mg/l at a temperature of 20° C. (If the level was above 5.0 mg/l, it was assumed the sample was sufficiently saturated with oxygen to proceed.) After oxygen saturation, the water was charged to a second vessel containing 8 grams of the dried granular PHENOBAC mutant bacteria containing Pseudomonas and 0.6 grams of potassium bicarbonate. The latter acted to buffer the pH in the vessel to approximately 7. A dissolved oxygen probe was then inserted into the vessel and the contents of the vessel stirred while measuring the dissolved oxygen concentration in the vessel. Several measured data points were recorded in one to two minute intervals for a period of about 30 minutes. These values were plotted with dissolved oxygen in mg/liter represented on the ordinant and time (minute) plotted represented on the abscissa. The baseline standard curves are shown as Curves A and J on FIGS. 1 and 2 respectively.

EXAMPLE 2

A series of tests was conducted for the purpose of determining the relative toxicity of various phenolic solutions. The general test technique involved the utilization of test samples containing various known concentrations of toxic material, e.g., phenol. The test sample was buffered to a pH of 7 by the addition of sodium hydroxide or sulphuric acid. Measurement of pH using pH paper was found most convenient. Once the pH of the solution was at the appropriate level, the sample was then aerated by placing the sample in a vessel half full of air, sealing the vessel and shaking the vessel vigorously for several minutes. The oxygen saturated 350 ml. solution having a dissolved oxygen content greater than 5.0 mg/l was then introduced to a test vessel containing 8 grams of dried granular PHENOBAC bacterial culture and 0.5 g of sodium bicarbonate. The dissolved oxygen concentration in the closed sealed vessel was then measured and plotted for a series of phenol concentrations in FIG. 1 in the same manner as the baseline standard in Example 1 and also illustrated in FIG. 1. Each curve, B–G, is labeled with respect to the phenol concentration present during the test. Curve A represents the baseline standard. From these curves one can calculate the rate of decline in dissolved oxygen concentration observed at 20 minutes for each phenol concentration. The percent inhibition is then calculated from the various dissolved oxygen decline curves for each phenol concentration in FIG. 1 according to the equation:

$$\% \text{ Inhibition} = \left[\left(1 - \frac{y/x \text{ dissolved oxygen decline each (phenol) sample (20 min.)}}{y/x \text{ dissolved oxygen decline baseline (20 min.)}}\right)\right] \times 100$$

The percent inhibition is a direct measure of the toxicity of the test solution on microorganisms. A 50% inhibition of the microorganisms is a representative value where appropriate diversionary action should probably be taken in a sewage treatment process. The reciprocal of the percent inhibition values as a function of the reciprocal of the phenol concentration to which the bacterial populations were exposed are recorded in graphically in FIG. 3.

EXAMPLE 3

Figure 2:
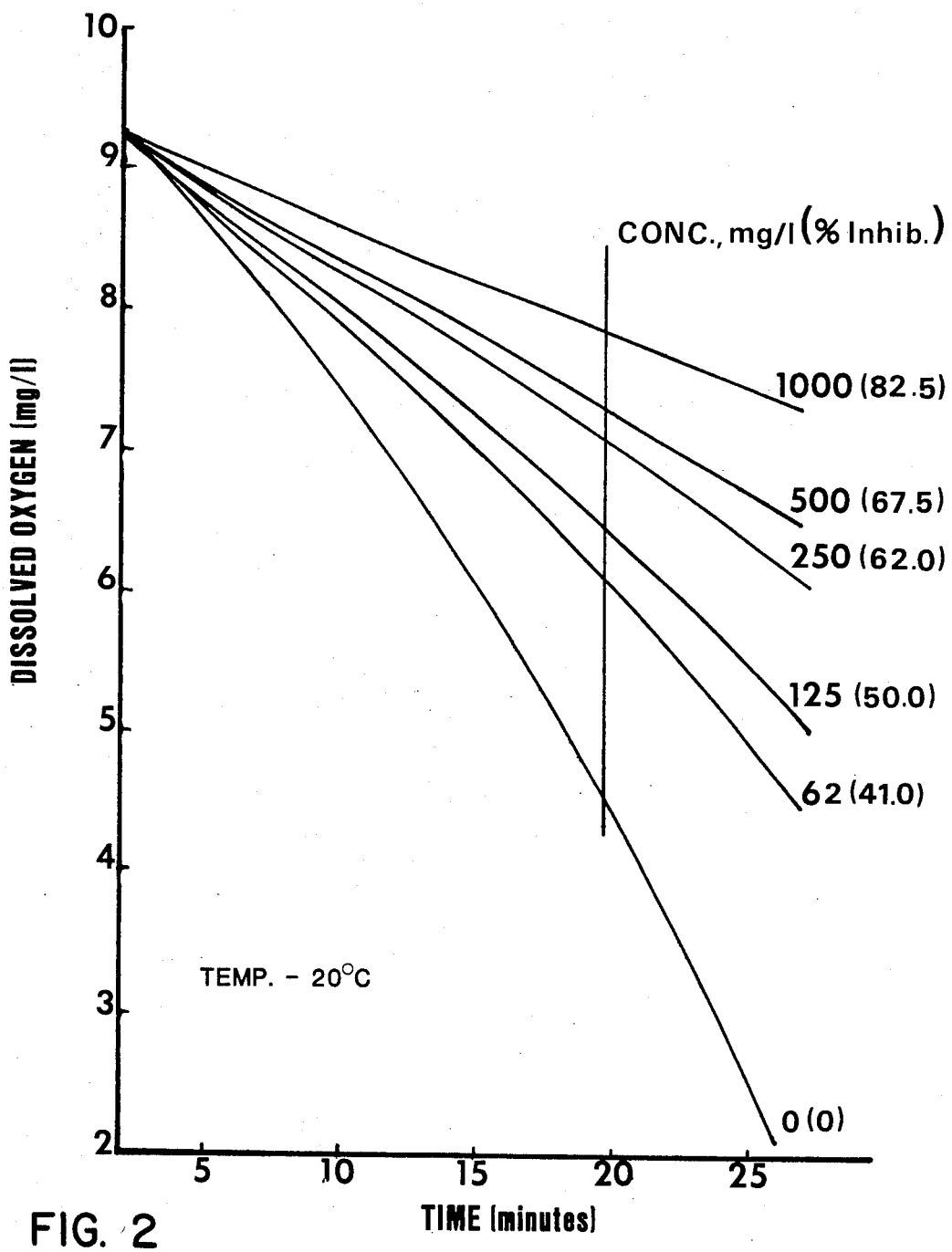
FIG. 2 is a plot of dissolved oxygen content as a function of time for aqueous systems containing various quantities of formaldehyde.

The procedure of Example 2 was repeated, except that formaldehyde solutions were substituted for the phenol solutions. FIG. 2 is a plot of dissolved oxygen content versus time for the formaldehyde solutions at various concentrations. The rate of decline was measured at 20 minutes and compared to the rate of decline for the baseline standard. The percent inhibition was calculated and the values, of 1/inhibitions were plotted against 1/concentration in FIG. 3. A similar test was also completed for copper (+2) ion solution.

From FIG. 3, it can be determined that concentrations of about 1600 mg/l of phenol, about 140 mg/l of formaldehyde, and 29 mg/l copper results in an inhibition of the bacteria of about 50%. If these concentrations were present in the incoming sewage in a sewage treatment plant, one could expect that the treatment plant operation could be substantially and adversely affected. Tests of the type disclosed herein on wastewater entering a treatment plant, however, could permit the plant operator to take appropriate action such as diversion to a spill pond if the toxicity of the incoming wastewater exceeded a preselected percent of inhibition.

EXAMPLE 4

To illustrate the increased sensitivity (for indicating toxicity) of the preferred method of contacting dehydrated or dried bacterial populations with the test solution as compared to non-dehydrated cultures the following series of tests were conducted. As in Examples 1 and 2, the general technique for these tests involved pretreatment of the wastewater or test solution to achieve a pH of 7.0 and an oxygen saturation of at least 5.0 mg/l. However, prior to adding the test solution to the test vessel containing the dried PHENOBAC culture, the bacteria were allowed to rehydrate 10 minutes in clean water and then the test solution containing phenol was added to the test vessel. In this manner, the initial rehydration of the bacterial populations was carried out in the absence of the chemical being tested. This is the customary prior art procedure. After rehydration, the bacteria were then exposed to the test chemical and its effect on bacterial respiration evaluated. The results are presented in Table 1 as percent inhibition observed at various phenol concentrations versus the percent inhibition observed without prehydration in the preferred (contact-rehydration) methodology. As can be seen, the bacteria showed greater inhibition or sensitivity when rehydrated in direct contact with the test phenol solutions rather than being rehydrated in water and then contacted with the test phenol solutions. The preferred methodology, therefore, provides a more conservative measure of inhibition than the clean prehydration method.

To summarize the examples, the methodology provides certain advantages over other methods known to the art. The test is rapid, requiring only 20 to 30 minutes in contrast to the 5 day BOD test. The test is conducted with reproducible bacteria cultures, thus avoiding use of bacterial cultures from an operating waste treatment plant which may vary in respiration and toxicity response characteristics from day to day. The test is conducted with simple laboratory apparatus and procedures. It is sensitive and accurate, therefore, the test can be applied to wastewater consisting of complex chemical mixtures. Because of the quickness in carrying out the test and because of its sensitivity, the operator is assisted in his judgment with regard to the toxicity of the incoming wastewater or chemicals without concern for the past history of bacterial populations obtained from an operating system.

TABLE I

| RELATIVE SENSITIVITY OF PREFERRED CONTACT-REHYDRATION METHODOLOGY | | |
|---|---|---|
| | PERCENT INHIBITION | |
| PHENOL CONCENTRATION (mg/l) | WITH PREHYDRATION | PREFERRED CONTACT REHYDRATION |
| 312 | 10 | 12 |
| 625 | 17 | 22 |
| 1,250 | 33 | 37 |
| 2,500 | 57 | 68 |
| 5,000 | 80 | 87 |
| 10,000 | 93 | 98 |

What is claimed is:

1. In a process for determining the quality of a wastewater solution or a solution of a specific chemical which comprises mixing microorganisms with a test solution, measuring the dissolved oxygen content in the test solution, and correlating dissolved oxygen content of the mixture with a standard solution, the improvement for enhancing the sensitivity of the test while reducing the amount of time necessary to conduct a test which comprises:
   a. utilizing a bacterial culture in the form of a dried powder, the bacterial culture being capable of aerobic biodegradation of organic wastes;
   b. placing a preselected amount of said bacterial culture into a test vessel containing a preselected amount of aqueous waste which has been saturated with oxygen;
   c. measuring the dissolved oxygen content in the test sample as a function of time;
   d. determining the rate of dissolved oxygen decline at a preselected time, and,
   e. determining the ratio between the rate of dissolved oxygen decline at said preselected time and the rate of decline for a preselected baseline standard solution, and thereby determining the degree of inhibition of bacterial respiration or growth.

2. The process of claim 1 wherein the bacterial culture contains an organism or organisms of pseudomonad, bacillus, aerobacter, azotobacter, arthrobacter, micrococcus, and nocardia.

3. The process of claim 2 wherein said dissolved oxygen content is measured at a preselected time within a range of 10 to 30 minutes or before the residual dissolved oxygen drops below 0.5 mg/l whichever is first.

4. The process of claim 3 wherein said microorganisms are combined with sufficient buffers to maintain a desired pH range during the procedure and said process is used to determine the quality of sewage containing phenol or formaldehyde.

5. The process of claim 1 wherein the quantity of preselected cultures employed is from 5 to 15 grams per 500 ml of sample solution.

6. The process of claim 5 wherein the bacterial culture employed is a mutant bacteria containing pseudomonads.

* * * * *